（12）United States Patent
Longmire et al.

(10) Patent No.: US 11,670,421 B2
(45) Date of Patent: Jun. 6, 2023

(54) METHOD AND SYSTEM ENABLING DIGITAL BIOMARKER DATA INTEGRATION AND ANALYSIS FOR CLINICAL TREATMENT IMPACT

(71) Applicant: Medable Inc., Palo Alto, CA (US)

(72) Inventors: Michelle Longmire, Palo Alto, CA (US); Ingrid Oakley-Girvan, Henderson, CA (US); Nick Moss, Los Alamos, NM (US); Reem Yunis, Menlo Park, CA (US); Anushka Manoj Gupta, Raleigh, NC (US)

(73) Assignee: Medable Inc., Palo Alto, CA (US)

( * ) Notice: Subject to any disclaimer, the term of this patent is extended or adjusted under 35 U.S.C. 154(b) by 0 days.

(21) Appl. No.: 17/219,867

(22) Filed: Mar. 31, 2021

(65) Prior Publication Data

US 2021/0375459 A1      Dec. 2, 2021

Related U.S. Application Data

(60) Provisional application No. 63/033,119, filed on Jun. 1, 2020.

(51) Int. Cl.
*G16H 50/20*       (2018.01)
*G16H 50/50*       (2018.01)
(Continued)

(52) U.S. Cl.
CPC ............. *G16H 50/20* (2018.01); *G16H 10/60* (2018.01); *G16H 20/00* (2018.01); *G16H 40/67* (2018.01);
(Continued)

(58) Field of Classification Search
None
See application file for complete search history.

(56) References Cited

U.S. PATENT DOCUMENTS

2001/0034615 A1   10/2001   Wilkinson
2007/0033072 A1   2/2007    Bildirici
(Continued)

FOREIGN PATENT DOCUMENTS

WO      2013036677      3/2013

OTHER PUBLICATIONS

Yoon et al, The Clustered AGgregation (CAG) Technique Leveraging Spatial and Temporal Correlations in Wireless Sensor Networks, ACM Transactions on Sensor Networks, vol. 3, No. 1, Article 3, 2007 (Year: 2007).*

(Continued)

*Primary Examiner* — Gregory Lultschik
(74) *Attorney, Agent, or Firm* — Cesari and McKenna, LLP

(57) ABSTRACT

The instant system and method will be a scalable and flexible software platform to agnostically capture wearable, implantable, or external device data and create a digital biomarker for various disease conditions, care and analysis. The system and method also provides an informatics tool for automated data aggregation, integration, and machine learning algorithms to uniformly compare/contrast/couple data streams as a function of patient and context over time. The focus is on user engagement and usability, accessibility and reporting to the clinical care team, and usability by researchers interested in analyzing data and outcomes.

16 Claims, 16 Drawing Sheets

(51) Int. Cl.
*G16H 50/70* (2018.01)
*G16H 40/67* (2018.01)
*G16H 10/60* (2018.01)
*G16H 20/00* (2018.01)
*G16H 70/60* (2018.01)

(52) U.S. Cl.
CPC ............ *G16H 50/50* (2018.01); *G16H 50/70* (2018.01); *G16H 70/60* (2018.01)

(56) References Cited

U.S. PATENT DOCUMENTS

| | | | |
|---|---|---|---|
| 2010/0268551 A1* | 10/2010 | Mcnames | G16H 50/70 705/3 |
| 2013/0080425 A1* | 3/2013 | Kwete | G16H 10/60 707/723 |
| 2014/0052465 A1* | 2/2014 | Madan | G16H 40/63 705/2 |
| 2014/0257852 A1 | 9/2014 | Walker | |
| 2016/0242690 A1* | 8/2016 | Principe | A61B 5/16 |
| 2017/0109475 A1* | 4/2017 | Kaditz | G16H 10/60 |
| 2017/0140119 A1* | 5/2017 | Laha | G16H 40/63 |
| 2017/0235894 A1* | 8/2017 | Cox | G06N 5/04 705/2 |
| 2017/0286622 A1 | 10/2017 | Cox | |
| 2017/0372029 A1 | 12/2017 | Saliman | |
| 2018/0113988 A1* | 4/2018 | Desgranges | G16H 40/20 |
| 2020/0152320 A1* | 5/2020 | Ghazaleh | G16H 10/60 |
| 2020/0303047 A1 | 9/2020 | Bostic | |
| 2020/0375544 A1* | 12/2020 | Naveh | A61B 5/112 |
| 2021/0142910 A1* | 5/2021 | Hafez | G16H 50/30 |
| 2021/0183518 A1* | 6/2021 | Karakaya | A61B 5/746 |
| 2021/0358627 A1 | 11/2021 | Longmire et al. | |

OTHER PUBLICATIONS

Nasoz et al., Emotion recognition from physiological signals using wireless sensors for presence technologies, 2004, Cogn Tech Work vol. 6, pp. 4-14 (Year: 2004).*

C. Stamate et al., "Deep learning parkinson's from smartphone data," 2017 IEEE International Conference on Pervasive Computing and Communications (PerCom), 2017, pp. 31-40, doi: 10.1109/PERCOM.2017.7917848 (Year 2017).

* cited by examiner

METHOD AND SYSTEM ENABLING DIGITAL BIOMARKER DATA INTEGRATION AND ANALYSIS FOR CLINICAL TREATMENT IMPACT

REFERENCE TO CROSS RELATED APPLICATIONS

The instant claims priority to U.S. Provisional Application 63/033,119 filed on Jun. 1 2020. We incorporate all the limitations of the provisional application in its entirety in this application.

STATEMENT REGARDING FEDERALLY SPONSORED RESEARCH OR DEVELOPMENT

This invention was made with government support under SBIR Grant No. HHSN261201800010C awarded by the National Institutes of Health. The Government has certain rights in the invention.

FIELD OF TECHNOLOGY

This present disclosure generally relates to a field of a method and system for utilizing a plurality of patients' wearable sensor data to generate analysis of digital biomarkers for improved clinical care impact.

BACKGROUND

Despite a growing digital marketplace, there are no commercial platforms to assess clinically relevant patient specific data at the population level. According to the American Cancer Society, in 2017 there were over 15.5 million Americans alive today who have been diagnosed with cancer or other long term diseases. This number of American diagnosed and living with cancer is expected to increase to over 20 million by 2026. Cancer survivors may experience a host of long-term and late effects that require coordinated care and self-management during and after completion of primary treatment for cancer. Yet, clinicians and researchers cannot harness the power of numbers using robustly collected patient specific data to provide early warning of pending treatment failure or disease recurrence and progression.

According to the "National Alliance for Caregiving" there is growing literature regarding the need for information delivery to cancer survivors and their caregivers as well as strong interest in improving clinical decision support (CDS) using validated clinical practice guidelines (CPGs). Currently the lack of comprehensive data, particularly ambient data collected outside of the clinical setting, limits researchers' abilities to optimize CDS through CPGs and also limits the ability of patients to benefit from these knowledge bases. There is a need to harness the power of technology and engage with the public to offer previously un-contemplated communication and information delivery to improve health care.

SUMMARY

Several embodiments for a method and system for a digital data integration and analysis for a clinical treatment impact as a scalable and flexible software platform that will facilitate harmonization and real-time analysis of patient data are disclosed. The digital biomarker data is gathered from diverse medical devices and commercial wearable devices for use in chronic-disease care and research, most notably for treatment of care of patients with cancer and other long term disease. In certain embodiments the disclosed system and method is designed to be agnostic as to the type of digital data it collects. In another embodiment multiple wearable device platforms can be incorporated to collect, analyze and report a wide variety of patient-generated data. A combined data of varied and its analysis of data helps clinicians and researchers to better understand disease and symptom progression through exquisite granular measurement of physical and physiological factors that exceeds currently used means in patient care.

In one embodiment the following methods that will be performed are:

Integrating biosensor data and digital data, monitoring for biometric data collection and passive monitoring plus carefully curated digital biomarkers for symptoms, side effects, quality of life indicators, and disease progression.

Predicting outcomes by analyzing using intelligent algorithmic capabilities that enable automated treatment recommendations based on patient digital biomarker and other data.

Communication management for providers, patients and researchers, physicians including a role-based configurable site dashboard in real time that includes trends and predictive analysis of digital biomarkers for symptom care and early notice in clinical trials of potential adverse event(s) or reduction in quality of life.

Regulatory Compliance: A product that complies with regulations and regulatory (e.g. FDA & EMEA and HIPPA) and data privacy requirements for clinical and research and trial settings Education & Information Content gathering: Information direct to patient or participant (DTP) about health and potential symptoms Disease-related information such as screening protocols for cancer early detection to be gathered using various platforms.

Patient Retention and Engagement Features to be performed by:
- Calendaring features with medication and trial visit reminders
- Capturing Patient notes
- Gamification of features
- Providing connectivity to digital communities
- Dashboards displaying relevant health data built upon the digital biomarkers.

In certain embodiments, the disclosed system and method includes safely collecting comprehensive clinical study patient information needed to make large advancements and improvement in managing chronic disease progression. Said clinical study patient information includes, but is not limited to individual patient's health and well-being. This clinical study patient information, which is derived from a plurality of sources, can be swiftly accessed and shared amongst relevant health professionals and medical researchers, wherein said clinical study patient information has the explicit intent of answering clinically relevant questions and improving CDS, which will result in improving patient adherence to medical treatment recommendations.

The foregoing and other objects, features and advantages of the present invention disclosed herein, as well as the invention itself, is designed to manage and alleviate co-occurring symptoms experienced by chronic disease patients. This involves the utilization of important factors including at least: a) accurate recognition and reporting of patient symptoms; b) removal of clinical barriers; and c)

patient adherence to recommendations. The disclosed system and method provides a means for medical researchers and clinicians to capture and analyze patient digital biomarker data, facilitating a much more accurate capture of information such as patient symptomatology. This removes clinical barriers such as time because clinically impactful digital biomarkers will be available to improve CDS. Thus, improving patient adherence to medical treatment recommendations.

BRIEF DESCRIPTION OF THE DRAWINGS

Example embodiments are illustrated by way of example and not limitation in the figures of the accompanying drawings, in which like references indicate similar elements and in which.

Others features of the present embodiments will be apparent from the accompanying drawings and from the detailed description that follows.

DETAILED DESCRIPTION

The increase in the number of cancer patients and survivors offers a vast pool of data that can be used to improve clinical knowledge and decision support. It also requires innovative, efficient and real-time strategies to improve care knowledge and delivery for true clinical impact and stakeholder buy-in. Using technology to measure, analyze and transmit knowledge to all stakeholders will improve clinical care, activate caregivers and engage patients in preventive health behaviors and treatment adherence. Better communication can lead to better health and wellbeing through early indicators of diminishing health, caregiver and patient empowerment, and by reduced burden and costs for clinical teams through improved management of routine symptoms and side-effects. The National Cancer Institute (NCI) and the Institute of Medicine (IOM) have called for major improvements in communication with patients, based on the beneficial effects of communication on quality of care and quality of life.

Management of patient treatment has increasingly relied on electronic monitoring. Current wearable data capture and analysis do not typically inform clinical knowledge and care. Consumers are rapidly adopting commercially available wearable technologies that facilitate continuous monitoring. However, there is a critical need for systems to integrate the data with objective statistical assessment of clinically relevant digital biomarkers. Such systems are needed to fully realize the power of these sensing technologies to promote: 1) knowledge regarding response to therapies; 2) symptom and side-effect reporting and management; 3) ability to discern ecologically valid clinical endpoints; and 4) early knowledge of real-time interventions to improve population health outcomes and reduce health care burdens.

Platforms that securely capture physical and chemical/biological sensor data across device vendors can serve as digital data warehouses for continuous, out of clinic, cancer research and patient assessment. This would facilitate novel direct and indirect measures of cancer development and progression with early warning to improve symptom and treatment related side-effect management. Moreover, such a platform also would be invaluable to compare experimental and conventional therapies and particularly to test novel classes of digital biomarkers that might signal success or distress and that might decrease the emotional and fiscal cost of clinical trials and care. In particular, there is a need for a clinically validated platform that is agnostic as to the data source and provides data harmonization with real-time analytics.

Figure 1:
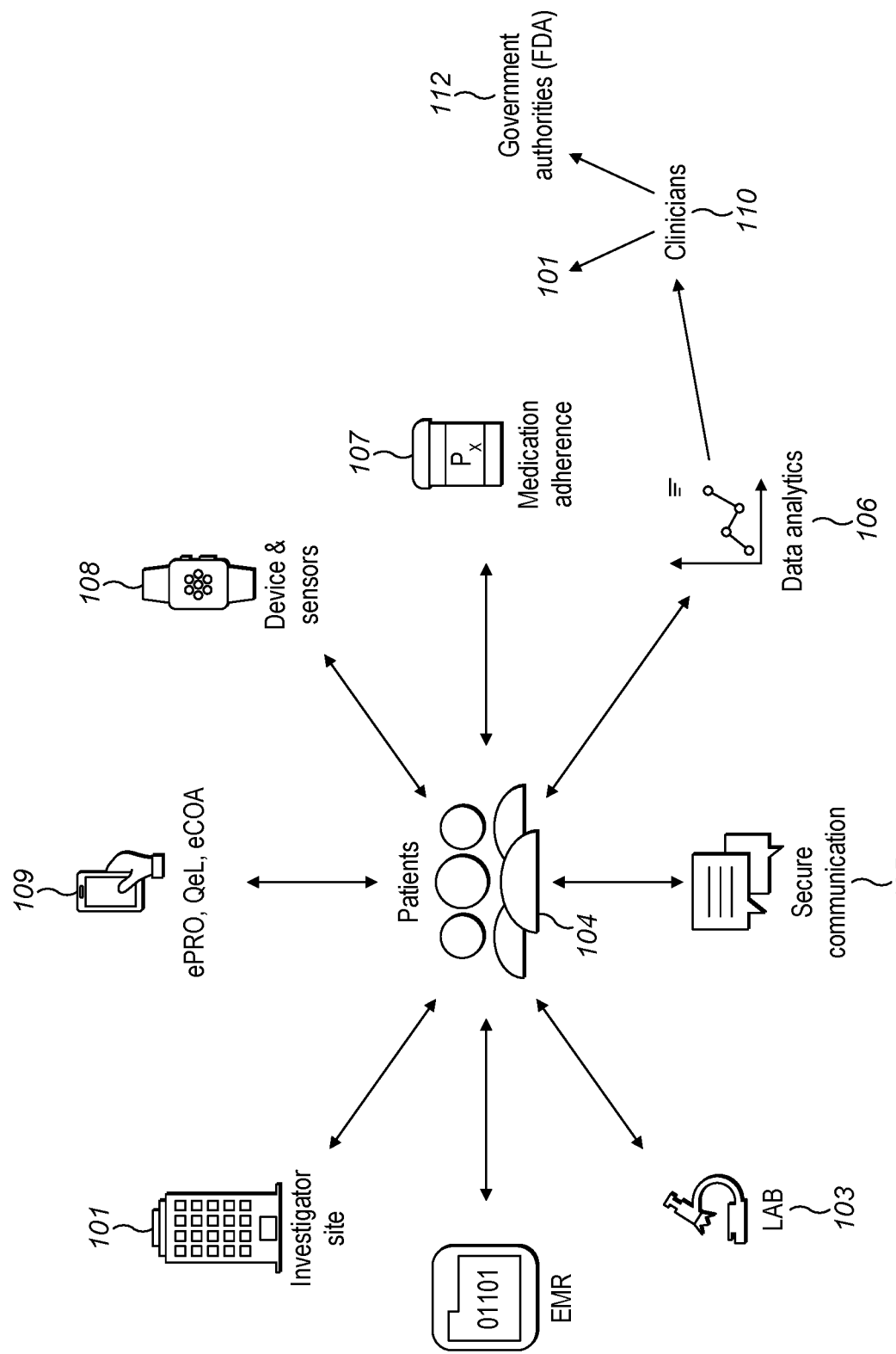
FIG. 1 shows the integrated digital biomarker application, method and system.

FIG. 1 shows the integrated digital biomarker use model. The use of integrated digital biomarker use model in FIG. 1 shows anticipated integration of the approach for maximal clinical impact and participant engagement/retention is critical. Because this model/tools reduce the time and cost for participants, compared to traditional clinical studies, they can increase participant recruitment and retention.

As research and clinical trials become more complex, participant recruitment and retention will remain a major challenge for researchers (101) and clinicians (110). Treatment can be demanding and frequent travel to clinical sites can deter participants from long-term participation in studies. One quarter of participants/patients (104) drop out before clinical trial study completion. In many studies, half or more of the follow-up visits could be relocated to a participant's home, especially if digital data are collected in a passive and continual manner. This added convenience and decentralization could substantially improve recruiting and retention. The ability to recruit and retain population-based samples and test digital biomarkers is even more critical in personalized medicine, in which genotype and phenotype help identify suitable therapies and predict prognosis. Patients (104) are recruited by investigator sites (101) their EMR(, lab (103), epro, qel, eCOA (109) are shared and given for data analytics (106) via a secure communication (105) along with their device and senor (108) data and their medication adherence data (107) recorded either by physicians or patients themselves. All these data for a specific trial or drug or patient is shared with government authorities or stake holders (112). If the stake holder is pharma companies they would know the outcome of a specific drug in real time due to the method and system deployed to gather a digital data integration and analysis performed for a clinical treatment impact in this description.

Figure 2:
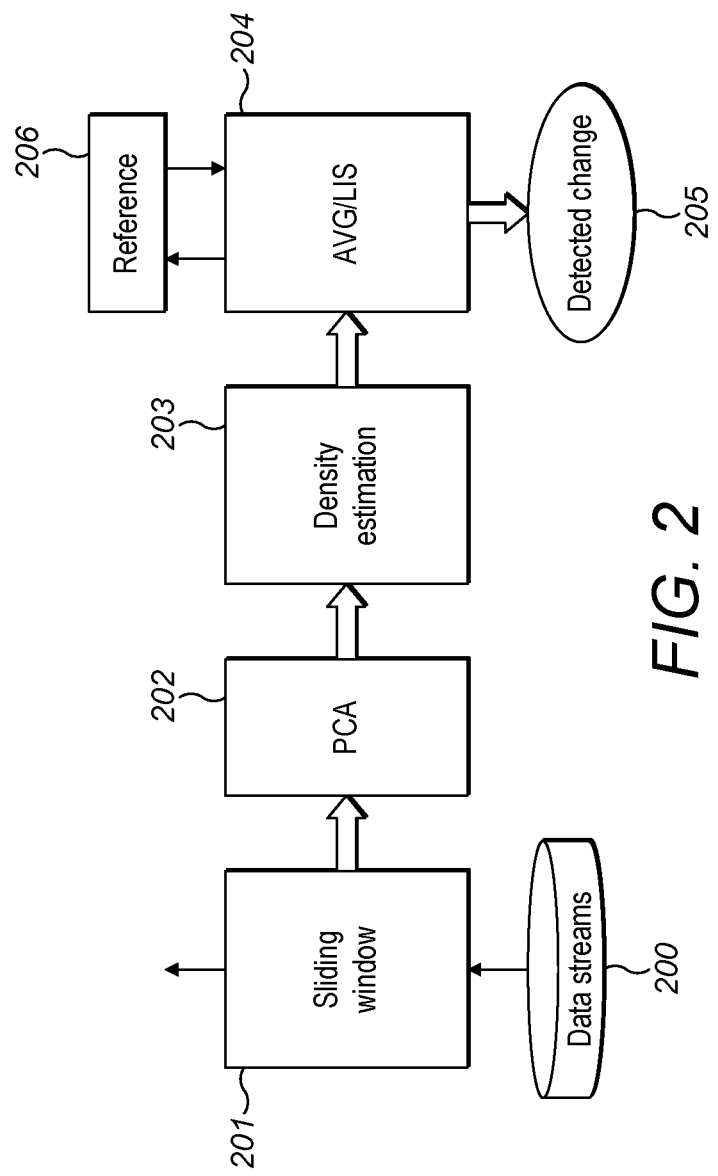
FIG. 2 shows a proposed framework for change detection in patient health.

FIG. 2 shows our proposed framework for change detection using a sliding window (201) for data streams (200). We expect to detect changes on transformed space using Principal Component Analysis (PCA) (202). A change in mean, variance and correlation on the original space is reflected in the transformed space. Using PCA also reduces the number of dimensions and therefore reduces the required computation. The system select the first k Principal Components (PCs) corresponding to large eigenvalues $\lambda i$ that satisfy:

$$i=1k\lambda i=1d\lambda i \geq 0.99 \qquad \text{Equation 1:}$$

where d is the total number of dimensions. At each window, the density will be estimated and the distance to the reference window that is used to build the model will be used to determine a change. To estimate density (203), we plan to employ KDE-Track. To measure difference between distributions, the systems use Symmetric KL-divergence (MKL) and Intersection Area Under Curves (IAUC), which were shown to offer higher accuracy. In each dimension i, the MKL and the IAUC between 2 estimated distributions are computed as follows.

$$\text{distanceMKL}(gi\|fi)=\max(dKL(gi,fi), dKL(fi,gi)) \qquad \text{Equation 2:}$$

$$\text{distanceIAUC}(gi\|fi)=1-x\min(fi(x),gi(x))dx \qquad \text{Equation 3:}$$

The distance between two windows with multidimensional data is the maximum of distances in dimensions. When data from the new distribution comes in, the system uses the W/S windows overlapping the two distributions. The distances to the reference window from these W/S windows exhibit 2 main properties: (1) The average value (204) of them is higher than the past (2) The length of the longest increasing subsequence increases. The system exploits these two properties by storing a number K of consecutive distances ($K \leq W/S$) in a buffer. When the window slides, the distance from the current window to the reference window is added to the end of the buffer. If the buffer is full with K values, the oldest value will be removed from the buffer before adding the new value. The buffer is then cleared after a change is detected. We propose using two algorithms to detect a change using the buffer K: DIM and LIS.

DIM: A change is detected (205) if the mean value of distances stored in the buffer is higher than the average distance from the beginning of the reference (206) window multiplied by a predefined threshold, DIM_th. Assume from the beginning of the reference window, there are count times the buffer is full and avgScore represents the overall average values of buffers. When the window slides, the distance to the reference window will be computed and added to the buffer. The average value of the distances in the buffer will be computed as: current $Avg = i=1KdiK$. In this approach, the system also monitors the average values of a number of consecutive distances to reduce the effect of signal spike.

LIS: DIM still has a disadvantage in that using a threshold based on the amount of change in distance and it is highly sensitive to the length of the longest increasing subsequence and is less sensitive than the amount of change. Specifically, for any magnitude of change, we have an increasing trend in the distances to the reference window. Therefore this can be applied to various magnitudes of change. Motivated by this, we propose LIS, exploiting the trend of increase of distances to the reference window when the distribution is changing. A change is detected when the length of the longest increasing subsequence of distances in the buffer is higher than a predefined threshold, LIS_th. An increasing subsequence can be formed by removing elements to achieve the remaining elements of the array that are in an increasing order. In Lee, the authors presented bounds for the average of $1n=1n!\partial\partial$ of maximal length $L(\partial)$ of an increasing subsequence of a permutation $\partial$ of n different numbers: With $n \geq 1$, $n \leq 1$ and $1n\sqrt{(n)} \rightarrow 2$ when $n \rightarrow \infty$. For a buffer with size K, the time complexity to get LIS of it is $O(K \log K)$.

The model, for example, eigenvectors and eigenvalues in PCA, will be built from the first window data. It will be used continuously as long as the data are generated in the same underlying distribution. Sensed data in Wireless Sensor Networks (WSN) will reflect the spatial and temporal correlations.

Figure 3:
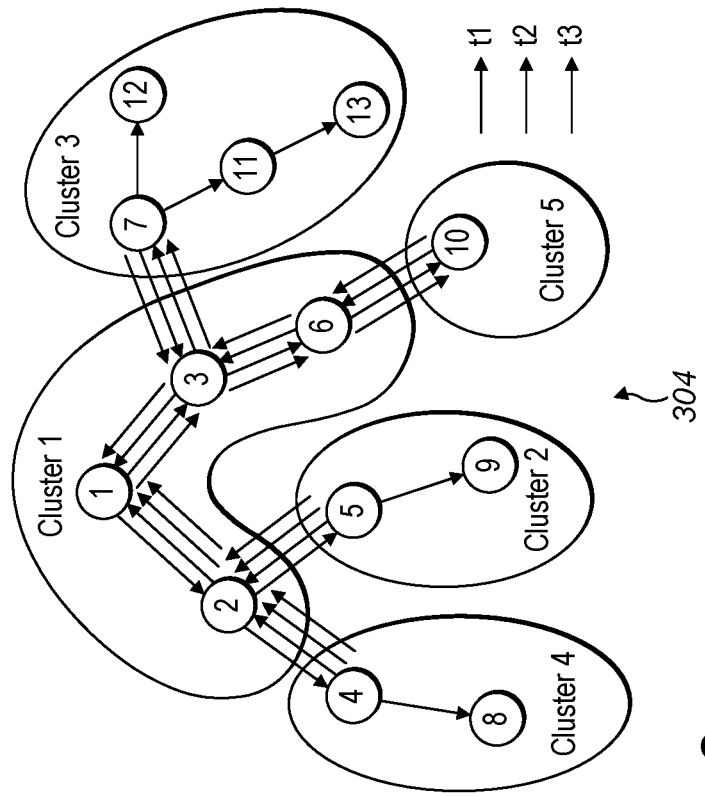
FIG. 3 shows two modes of Clustered AGgregation (CAG) operation calculations.
Figure 3:
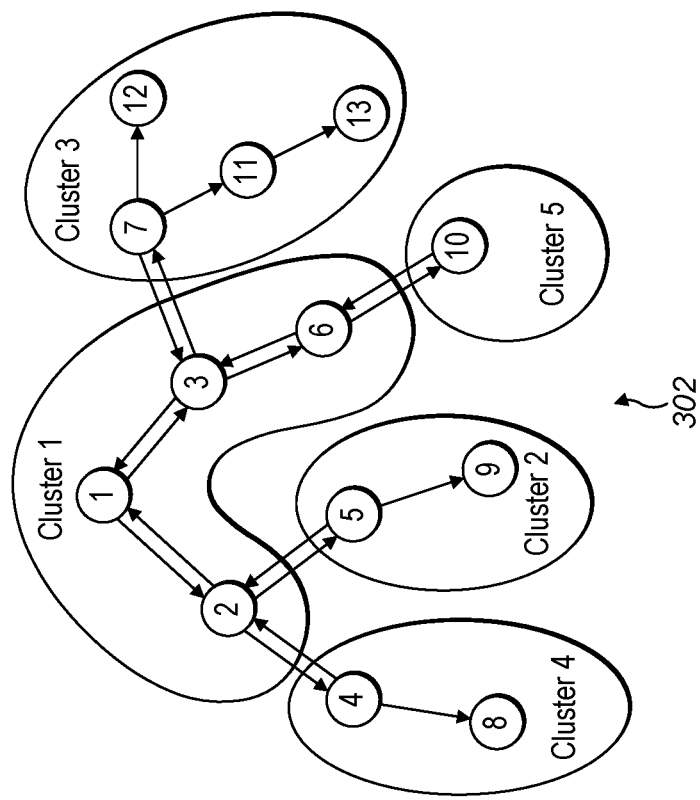

FIG. 3 shows two modes of Clustered AGgregation (CAG) operation: interactive (302) and streaming modes (304). The solid lines indicate the query propagation and the dotted lines indicate the response. Black nodes are cluster heads, gray nodes are bridges, and white nodes are non-participating nodes.

Correlation Identification: So far we discussed how to detect changes in the streaming data and only transmit the changes to the servers. The system also works on how to identify the correlations between different mobile devices. Our main goal is to reduce the overhead of data collection and hence save battery power in the mobile devices. In particular, the system develops a CAG algorithm that forms clusters of nodes sensing similar values within a given threshold (spatial correlation), and these clusters remain unchanged as long as the sensor values stay within a threshold over time (temporal correlation). With CAG, only one sensor reading per cluster is transmitted whereas with Tiny AGgregation (TAG) all the nodes in the network transmit the sensor readings. Thus, CAG provides energy efficient and approximate aggregation results with small and often negligible and bounded error. In our previous research, we have developed a CAG framework that can save 68.25% of transmissions over TAG with only 2.46% inaccuracy in the result. We showed that the streaming mode of CAG will save even more transmissions (up to 70.24% in our experiments) over TAG, when data shows high spatial and temporal correlation.

In this invention, an extension of algorithms is done in various methods. a) the integration and deployment of our algorithm in the mobile phone application framework. b) The system investigate the effectiveness of CAG that exploits the temporal as well as spatial correlations using both the measured and modeled data. c) The system design CAG for two modes of operation (interactive and streaming) to enable CAG to be used in different environments and for different purposes. In particular, depending on the application's requirements, CAG can work in two modes: interactive and streaming. CAG generates a single set of responses in the interactive mode. In the streaming mode, periodic responses are generated in response to a query. The interactive mode of CAG exploits only the spatial correlation of sensed data, whereas the streaming mode of CAG takes advantage of both spatial and temporal correlations of data.

FIG. 3 shows the cluster-head responding with a single value in the interactive mode (302). FIG. 3 (304) shows periodic response messages from cluster-heads in the streaming mode. We plan to run CAG algorithms in two phases: query and response. During the query phase, CAG forms clusters when a TAG-like forwarding tree is built using a user-specified error threshold $\tau$. In the response phase, CAG transmits a single value per cluster. CAG is a lossy clustering method in that only the cluster-heads contribute to the aggregation. Finally, we plan to develop a fixed range clustering method, which makes the performance of the system independent of the magnitude of the sensor readings and the network topology.

Figure 4:
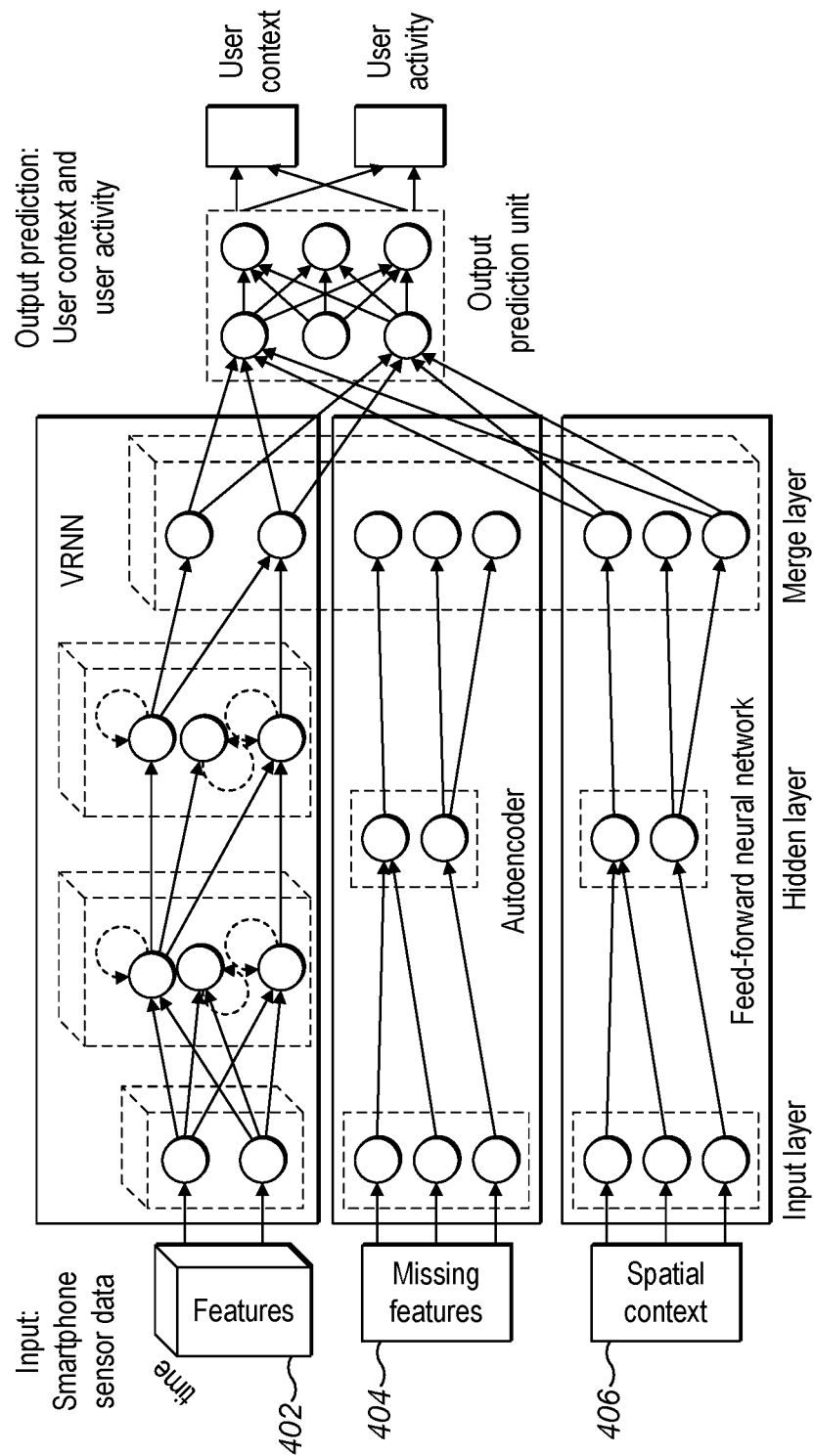
FIG. 4 shows a proposed model of a deep ensemble model for Context and Activity Recognition.

This project will explicate and address these drawbacks and will efficiently use all the sensors present on the smartphone device or consider all the variables needed through multiple sensors. Some of our Project Team Advisory Group have proposed developing Deep Ensemble model for Context and Activity Recognition (DE-CAR) which jointly recognizes the user context (i.e. where the sensor data was collected from) and more than 25 user activities (e.g., walking, sleeping, talking in car, running, driving, etc.) based on the smartphone sensor data. DE-CAR framework is an ensemble of various deep models that share an output prediction unit. The modeling pipeline ensembles the predictions of multiple kinds of neural networks are shown in FIG. 4. These take unique feature inputs (the "Input layer"), process them in parallel (the "Hidden layers"), and merge the results ("Merge layer").

User time-series features (402) are processed temporally in both generative and discriminative fashions. The temporal modeling can be pre-trained on a related task, with internal features extracted—for example, generative temporal models like VRNN, WaveGAN, or LSTM-VAE can model the underlying distribution of the time series, while discriminative temporal models like some RNNs, transformers, or convolutional networks can attempt to forecast future values or classify some relevant state. Alternatively, the modeling can be trained "in-the-loop" alongside the downstream predictions of the user state, providing temporal structure to the prediction problem.

Features missing from the data-collection pipeline are inferred through the use of variational autoencoders (in what may be considered a lower-dimensional analogue to image inpainting). This preserves information during model training and at test-time (404). Spatial context—feature volumes derived from image inputs, using upstream convolutional neural networks—are further processed in a feed-forward fashion and appended to the other features. Relevant spatial context can consist of a variety of representations, including (but not limited to) a convolutional autoencoder's latent representation or the features of a classification network trained to solve a related problem (406). Finally, all of these prior levels of modeling and the features derived from them are merged and used as inputs to a final prediction of user context/state and the current user activity.

DE-CAR utilizes Variational Recurrent Neural Network (VRNN) models to capture the complex temporal dependencies present in different sensor data, utilizes deep autoencoder to handle missing sensor data patterns, and uses the feed forward neural networks to model the spatial context extracted from the FOVs. The missing patterns such as how long the data has been missing and since when and where it is missing are informative. The representations learned by VRNN, autoencoder and feed-forward neural networks will be merged in a shared representation layer, which is then connected to the output prediction unit, which consists of multiple layers of feed-forward neural networks, to jointly identify the user context and the user activities. The DE-CAR framework will be efficiently trained using several good deep learning practices including batch normalization, mini-batch training, Adam optimizer, dropout, and early stopping and regularizations.

The proposed model DE-CAR assumes that the context and activity labels will be available along with the input sensor data to perform context and activity recognition. However, obtaining human annotated labels to all the sensor data is expensive and infeasible. On the other hand, recent research showed that we can build deep models on a small well-annotated dataset while also using a lot of unlabeled data. Thus, we propose Semi-Supervised Generative Models for Holistic Activity Modeling, where the semi-supervised models will be built on top of the proposed DE-CAR deep learning framework.

Semi-supervised Deep Generative Models for Holistic Activity Modeling: Manual annotations of vast amounts of data collected over time on mobile devices are prohibitively expensive, yet the abundantly collected data can be leveraged using either entirely unsupervised or semi-supervised modeling approaches. Dynamic Semi-supervised Generative Models will improve learned representations of continuous cell phone or sensor data. Some of the most successful deep learning techniques fall under the category of Generative Models. Using Generative Models, such as Variational Autoencoders or Generative Adversarial Networks, it is possible to learn representations from both (scarce) annotated and (abundant) unlabeled data to solve for example challenging human behavior recognition tasks. While these models have been utilized successfully for a wide range of tasks, some considerable challenges remain. In particular, these challenges exist with respect to generative sequence modeling and multi-task learning. For expanded bioinformatics methods, we propose to develop a semi-supervised deep generative modeling framework for activity recognition using a dynamic architecture that combines both generative capabilities (unsupervised) as well as discriminative capabilities (supervised).

Specifically, we propose to develop a semi-supervised deep generative model that is jointly trained with a DE-CAR framework for activity recognition. This approach extends prior work for end-to-end human affect recognition that leveraged large quantities of unlabeled speech data together with a smaller dataset that was manually annotated. Specifically, the proposed model dynamically encodes the continuous cell phone data using a dynamic RNN encoder-decoder architecture and extends adversarial network architectures to generate sequence data rather than static representations. Following this strategy we expect that it will be possible to learn dynamic representations with higher discriminative faculty than using standard feature extraction or machine learning approaches, which cannot take advantage of large quantities of unlabeled data.

If available through collaboration with NCI or third party sources, the system trains the proposed semi-supervised deep generative model with annotated human activity data recorded in a controlled environment and complement the training with large quantities of unlabeled data. The variational recurrent neural network capable of encoding dynamic sequences will be trained end-to-end. The proposed models will be both trained offline and integrated in the proposed real-time pipeline for activity recognition. The system will rigorously evaluate the performance of DE-CAR and Semi-supervised deep generative models and benchmark performance with the current state-of-the-art models. For prediction tasks, the system examines the Area under ROC curve (AUC) as well as the accuracy, F1-score, precision and recall.

Figure 5:
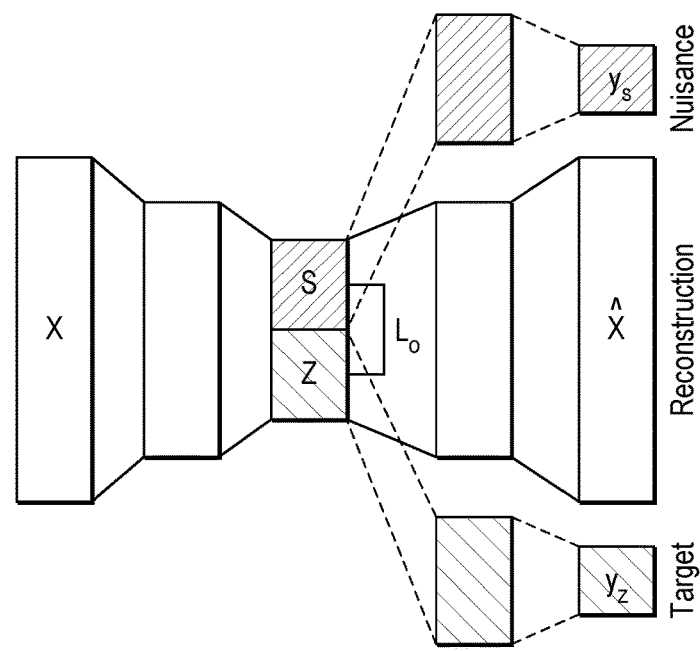
FIG. 5 shows schematic view of model with nuisance subspace s and target subspace z.

FIG. 5 shows schematic view of model with nuisance subspace s and target subspace z. There are important aspects such as Nuisance-free Representation Learning for Improved Context and Activity Classification. If available through NCI or third party sources, we plan to leverage population, long-term sequential and extensive context information to remove factors of variation related to nuisance variables to improve both context/activity classification and enable medical condition prediction. Successful activity recognition within unconstrained data collections necessitates the removal of factors of variation that pertain to nuisance variables (e.g., the context of activity, noise, device specific sensor characteristics, etc.) to improve signal to noise contrast of weak activity specific signals. We propose a novel approach, namely Nuisance-free Representation Learning to effectively solve this problem.

Representation learning strategies, in general do not require additional information about the data to learn meaningful representations, however, they can benefit from additional constraints that limit the dependency on so-called nuisance variables. When learning representations of, for example, paralinguistic characteristics of emotional speech it might be beneficial for the model to know if the speaker is male or female, as a number of voice characteristics are strongly dependent on gender due to (among other factors) anatomical differences. Hence, one might consider gender a nuisance when attempting to learn representations of affective human behavior or spoken word embedding. The direct modeling of the situational context (e.g., driving in a car, sitting at desk, etc.) can help amplify the signal strength of the latent target behavior or condition to enable early predictions. Specifically, the system develop statistical models and extend current approaches that explicitly learn nuisance-free representations of collected multimodal data. We hypothesize that by separating salient factors from noise/nuisance factors, a better representation of the target activities can be obtained from the latent embedding.

In one embodiment it is proposed to evaluate the performance of the proposed nuisance-free model and compare it to the generative models without the nuisance-free learning components as our baseline models. The system evaluate the performance of the neural networks using a range of metrics including accuracy, precision, recall, and F1-score for fair comparisons and measure delta improvement with respect to baseline performance. Further, the system compare model performance on the activity recognition tasks for both the learned nuisance space representations and target space representations to ensure that the model learns desired characteristics. For example, The system test whether the model performs poorly on the nuisance variables (since factors pertaining to nuisance variables were removed from the signal) while it improves performance on target behaviors.

Multimodal Representation Learning: Cellphone sensors and others can produce data of varying modalities (e.g., accelerometer, microphone, camera, etc.) that capture user activities and states with varying dynamics. We propose to establish Multimodal Neural Alignment Models to derive multimodal behavior representations and potentially reconstruct noisy or missing sensory data using cross-modal generation.

Human activities and communication are often interplay between spoken words, facial expressions, and gestures. It is often necessary to fuse all complementary sources of information to be able to fully understand context and recognize activities. Frequently, these multimodal cues are correlated in obvious ways, for example, an utterance with laughter sounds is more likely to have words colored with positive emotion and is accompanied with specific facial expressions and movements. These occurrences of multiple cues, all of which are indicative of the speaker's affective state or activity, can improve learned representations.

Multimodal representation learning has been the subject of several investigations. However, a number of open challenges need to be addressed to build models that can learn correlations between for example spoken words and non-verbal speech features, facial expressions, or other sensory information such as accelerometer data while communicating. Our prior investigations into enhancing for example human performance recognition and neural language modeling showed significant improvements over the unimodal baselines. From a language modeling perspective, for example, the inclusion of extra-linguistic information resulted in an average 2% improvement in model perplexity on a speech corpus comprising over 2000 h of data.

Following the distributional hypothesis, which states that certain behaviors or events which occur in the same contexts tend to have similar meanings or outcomes, it can be hypothesized that multimodal units (such as prosody of speech, sensory data, or accompanying facial expressions) which co-occur can often carry additional information to either improve activity recognition, or can also be utilized to reconstruct missing data in another modality.

Figure 6:
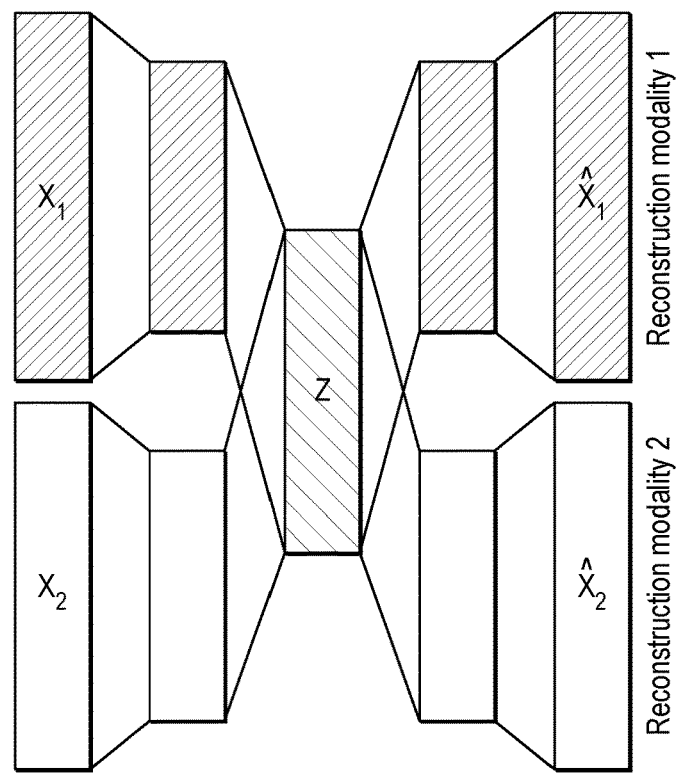
FIG. 6 shows an example of multimodal generative architectures.

It may be possible to expand the generative models and nuisance-free representation learning approaches by incorporating information from multiple modalities to form holistic assessments of user activities and information from the cell phone. Specifically, and depending upon the available data and decisions by the team in conjunction with NCI regarding approach and time commitment, we could approach multimodal integration by aligning signals across the available modalities through the use of dynamic encoder-decoder architectures that share representations across modalities (depicted in FIG. 6). Previous multimodal behavior analysis typically regards each modality as an independent information source. However, specific communication and physical activity patterns are often strongly correlated, and co-analyzing them can significantly improve the accuracy of recognition and prediction. For example, we show that extra-linguistic information can significantly improve language modeling performance and helps the neural network disambiguate between multiple hypotheses.

In order to complement the proposed generative models with additional input sources. For example, the system complement microphone data with accelerometer information to better represent users' activities. The information from multiple modalities in such multimodal generative architectures receive multiple inputs from different sensors as input and learn shared representations in one or more shared multimodal representation layers. While the depicted architecture in FIG. 6 only fuses two modalities, the approach is not limited by the number of modalities.

The system compares these learned multimodal behavior representations to the proposed uni-modal representation learning approaches and assess what the value added of each additional modality is to the representation. Value added will be expressed in delta improvement of proposed evaluation metrics (e.g., F1-score, precision, recall, and AUC). Apart from evaluating the discriminative faculty of the learned multimodal behavior representations, we also plan to evaluate models' capability to reconstruct one modality's signal from the other's in cross-modal generation experiments if such data exists. Following this strategy, it might become possible to recover missing or noisy signal modalities that could provide essential information for clinical condition prediction or user activity recognition. Cross-modal reconstruction performance could be evaluated in root mean square error of reconstructed signal as well as measures such as concordance correlation coefficients measuring both correlation between reconstructed and target signal as well as mean deviation.

Methods. The system collect information from users of the mobile application through surveys. Survey frequency and questions are defined by the health expert for the application. Surveys capture patient reported information (Screenshot 1) including but not limited to:

Symptoms

Side effects

Quality of life measures

Other

The method and system should provide automated file transfer screening and database importation protocols for clinical grade medical devices, wearables, and sensors for biometric data collection and passive monitoring. The system use well platform and system protocols established in the computer science arena to conduct beta-testing and finalize specific elements of the product. For evaluation and expected outcomes: The current system platform is designed to capture, analyze, and visualize device data in real-time and to enable alerts and notifications from real-time continuous device data monitoring through the current system and method Insights and Alerts.

Figure 7:
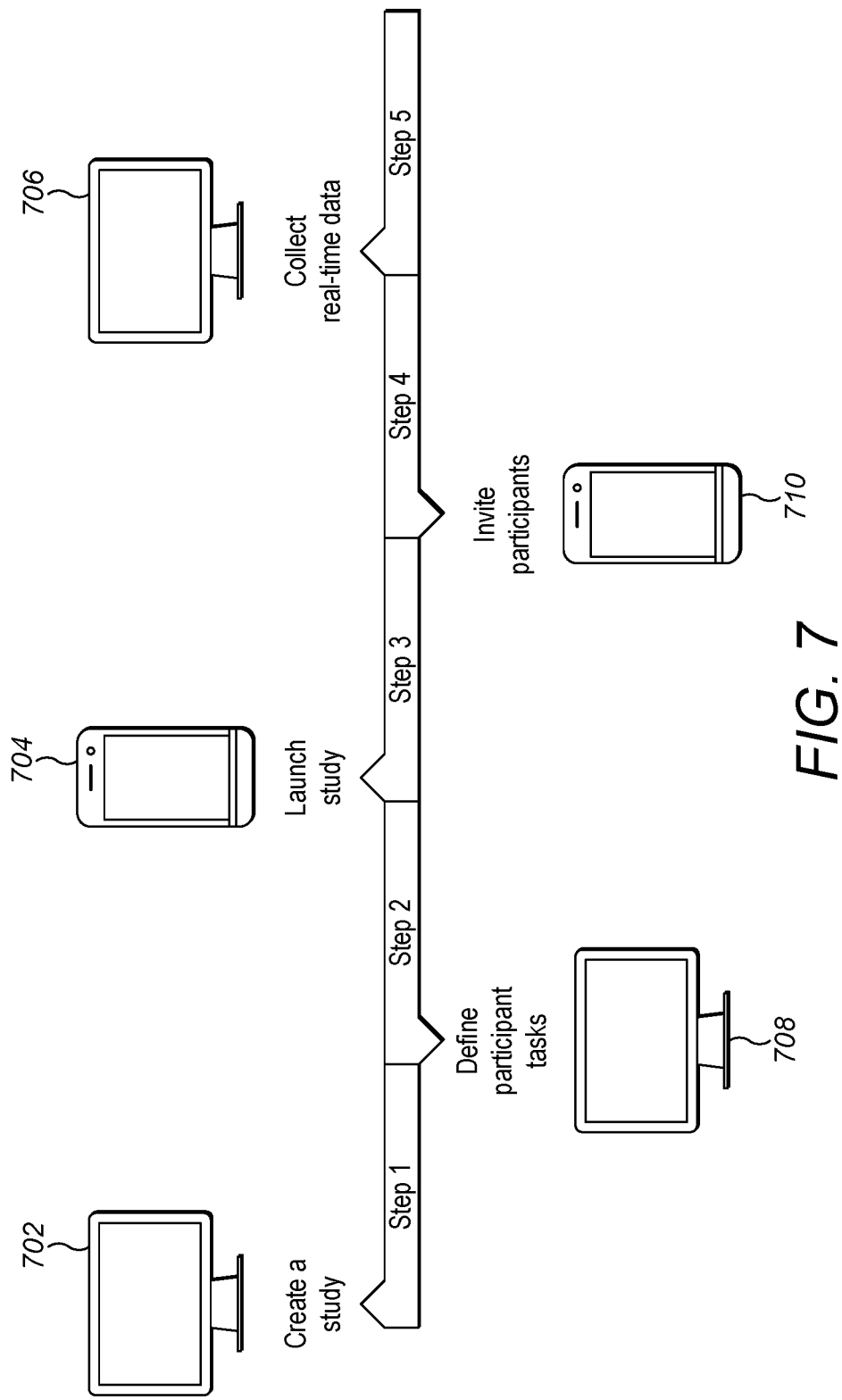
FIG. 7 shows creating a research or clinical trial mobile app using Cortex.

In this project the system operates from a "Bring Your Own Device (BYOD)" model. The platform-as-a-service (FIG. 7) can be configured to enable any connected device for in-app data sharing, tracking, and trending by mobile application users (704), analytics across individuals or the entire patient cohort, and algorithm driven alerts and notifications.

Figure 8:
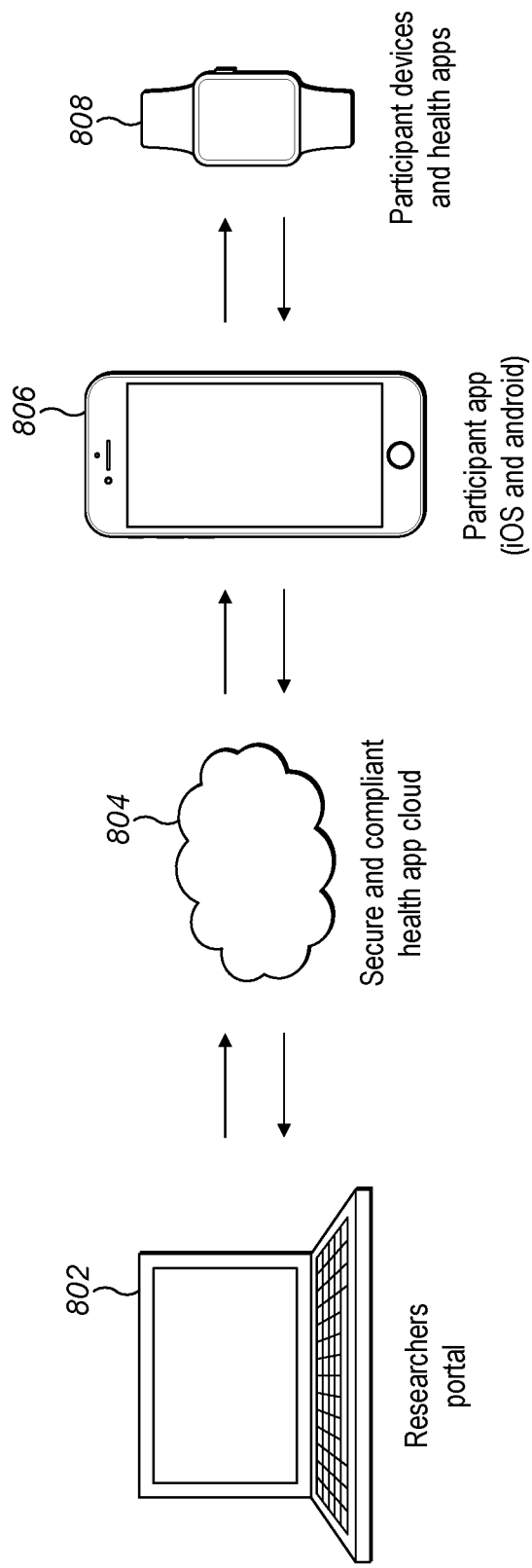
FIG. 8 shows the current system and method to connect various devices.

FIG. 8 shows Patient health data is collected on various devices (808) and aggregated on the participant app (806), which communicates with the secure and compliant health app cloud system (804). From this cloud, the data can be accessed by researchers through the researcher portal (802).

Figure 9:
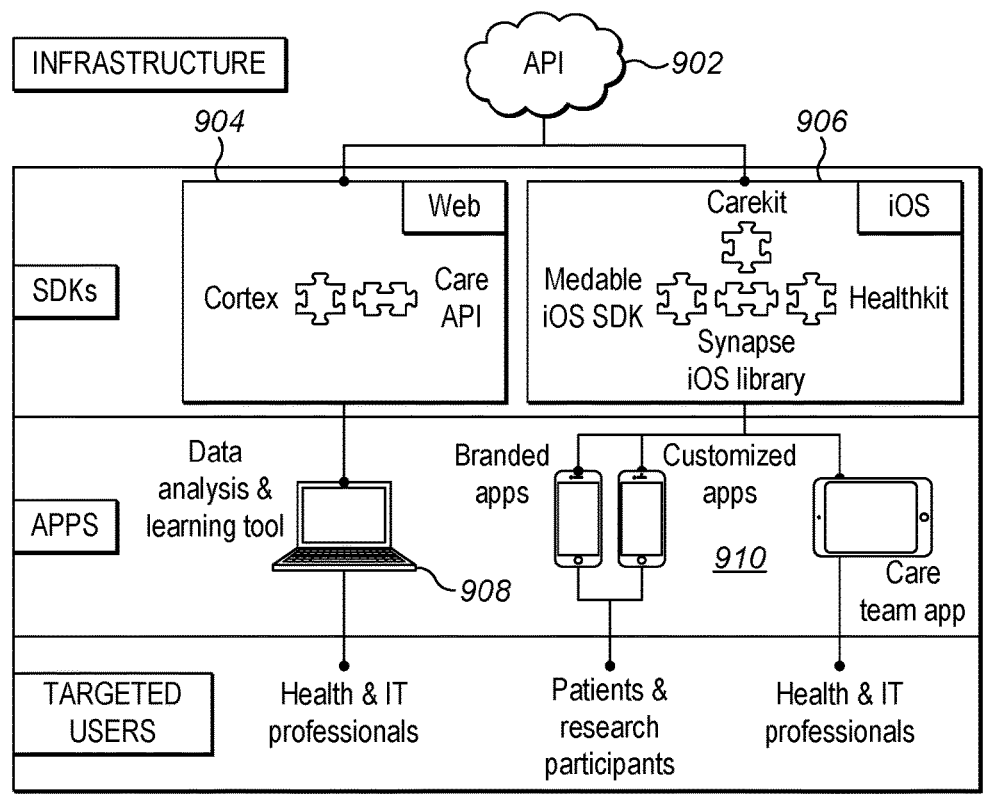
FIG. 9 shows the detailed architecture of the infrastructure.

FIG. 9 shows instant system's API (902) enables the creation of both web-based and mobile SDKs (904, 906). These SDKs in turn enable the creation of software (908) and mobile apps (910) used by health professionals and patients. For example, the web-based Care API interfaces with the Cerebrum machine learning (904) engine to create a web app for data analysis and learning by health and IT professionals (908). Similarly, instant system's mobile SDKs (906) support the creation of both branded patient-facing mobile apps and a care-team app for health professionals (910).

Figure 10:
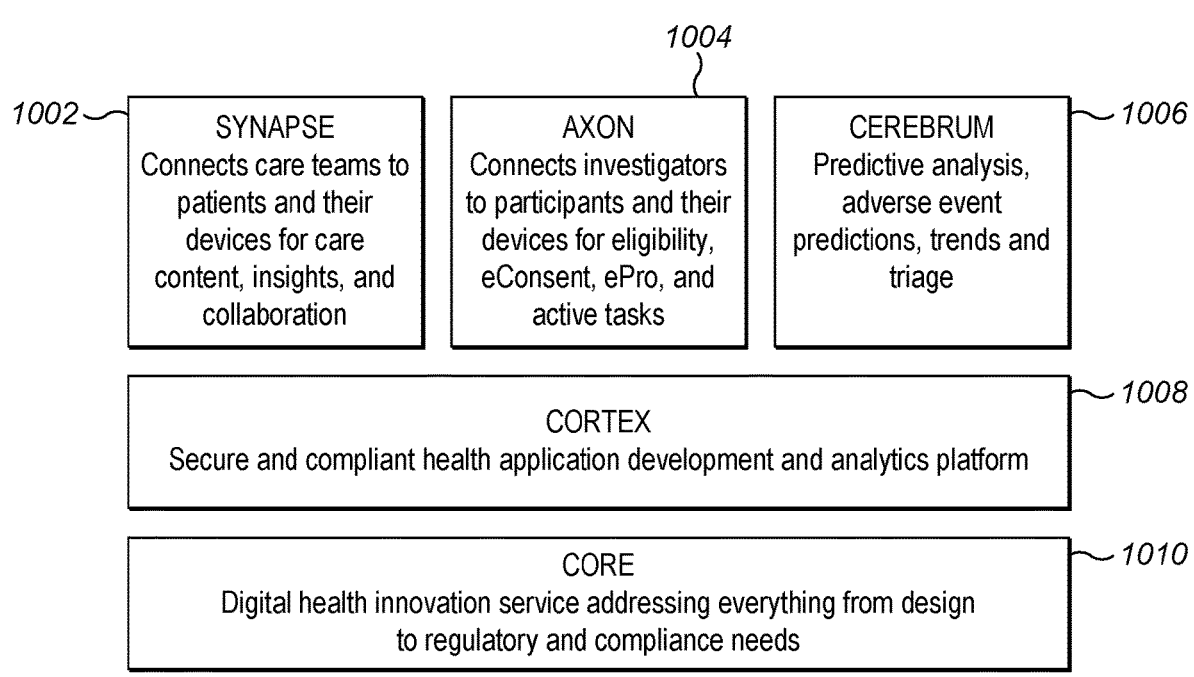
FIG. 10 shows the application layers in the system.

FIG. 10 shows the system layers. The core of the instant system Axon (1004) and Synapse (1002) products are designed to gather data from Apple's HealthKit and the Google Fit Store with extension to other sensor devices through Cortex. This system's experience in gathering health data includes all sensor data defined below and all health data collected by connected health devices such as an Apple Watch or Fitbit, using tools such as ResearchKit, ResearchStack, HealthKit and Care Kit. When a user provides permission for an app to read and write health and activity data, the system and method can become a valuable health data source.

Cortex (1008) can be used to configure the mobile app and the "how it works" is displayed in this schematic providing a study overview for the researchers portal to creating a mobile app for a study using Cortex. FIG. 9 shows creating a research or clinical trial mobile app using Cortex. Our system and method shows we include digital biomarker data captured from biosensors into Step 2 where participant tasks or data is configured that is provided at a high level in FIG. 10. FIG. 10 shows linking the Cortex created mobile App with device data for digital biomarker capture. The core (1010) performs the function of digital health innovation service addressing everything from design to regulatory and compliance needs. Cerebrum (1006) performs predictive analysis, adverse events predictions, trends and triage.

Figure 11A:
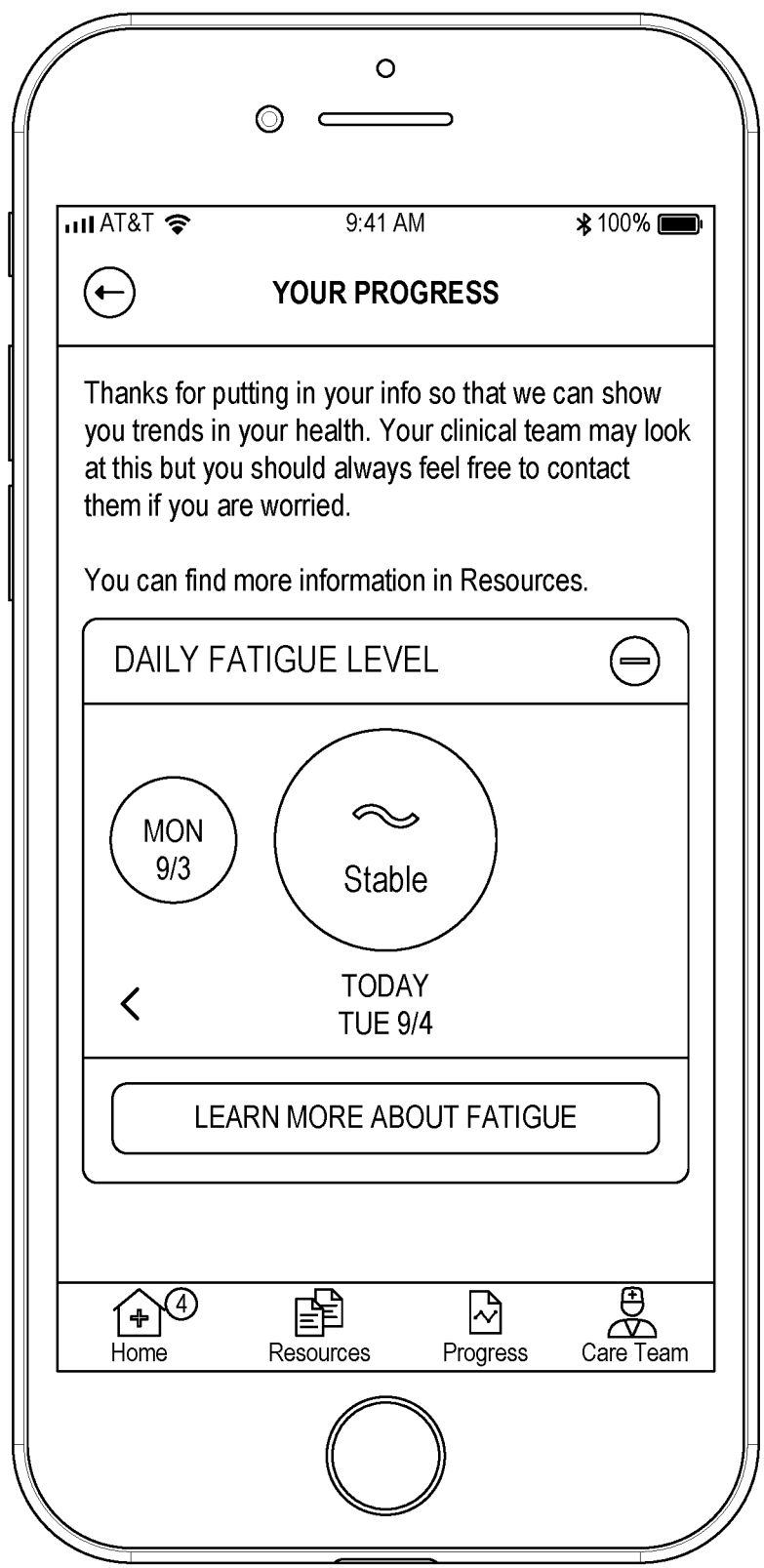
FIG. 11A and FIG. 11B shows patient mobile phone view of their progress.
Figure 11B:
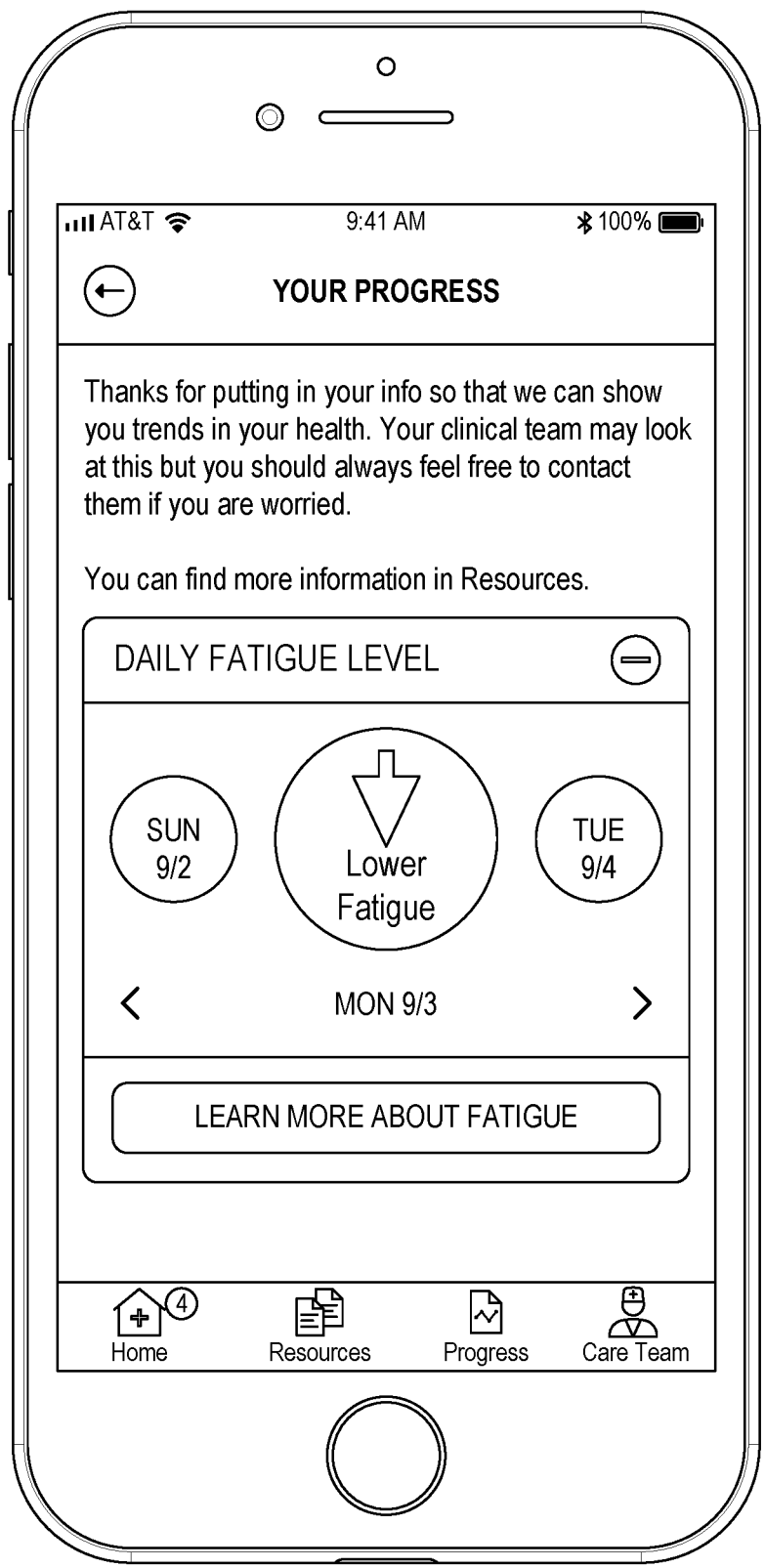
Figure 12:
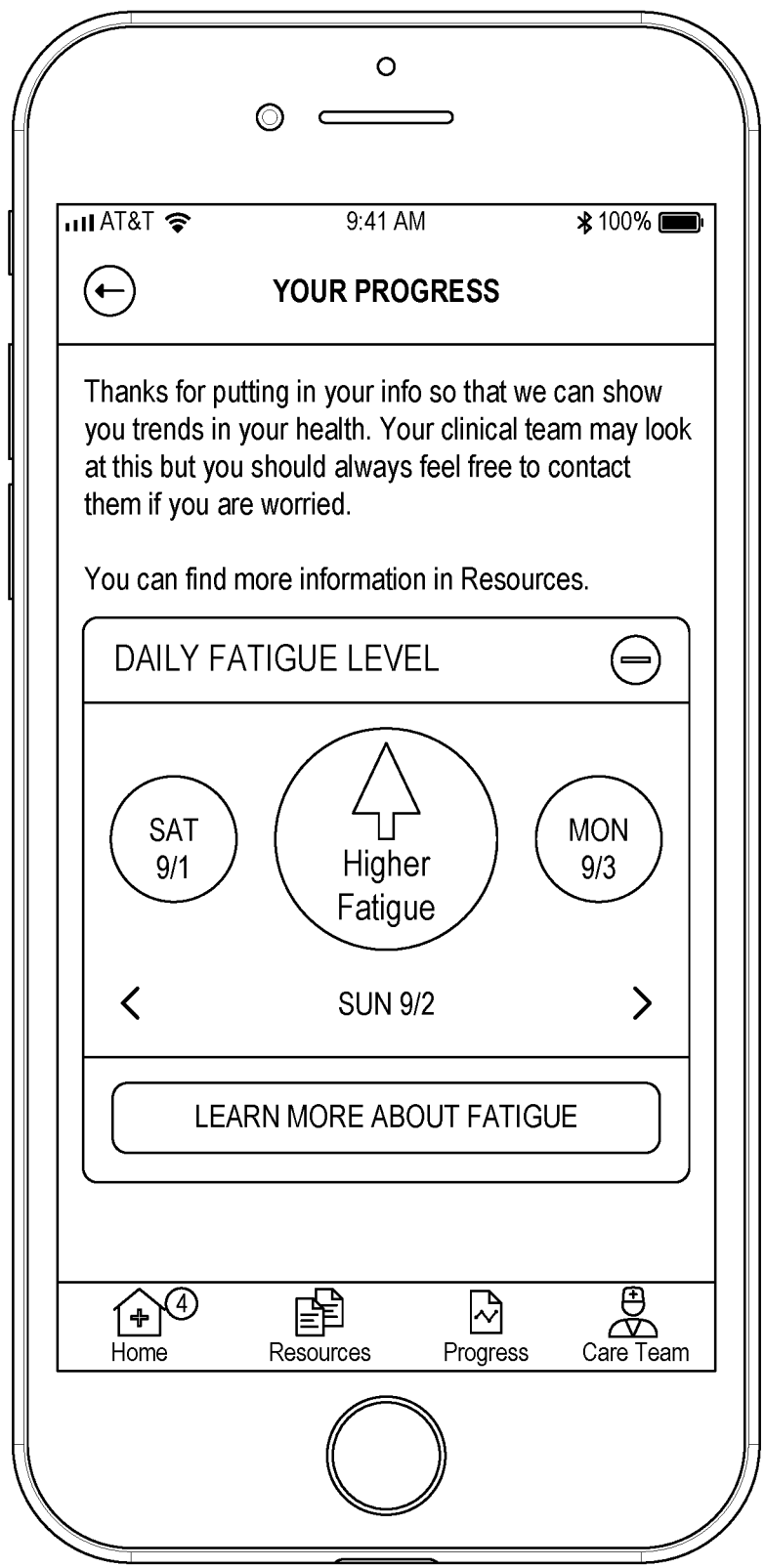
FIG. 12 shows yet another embodiment of the patient progress level.
Figure 13A:
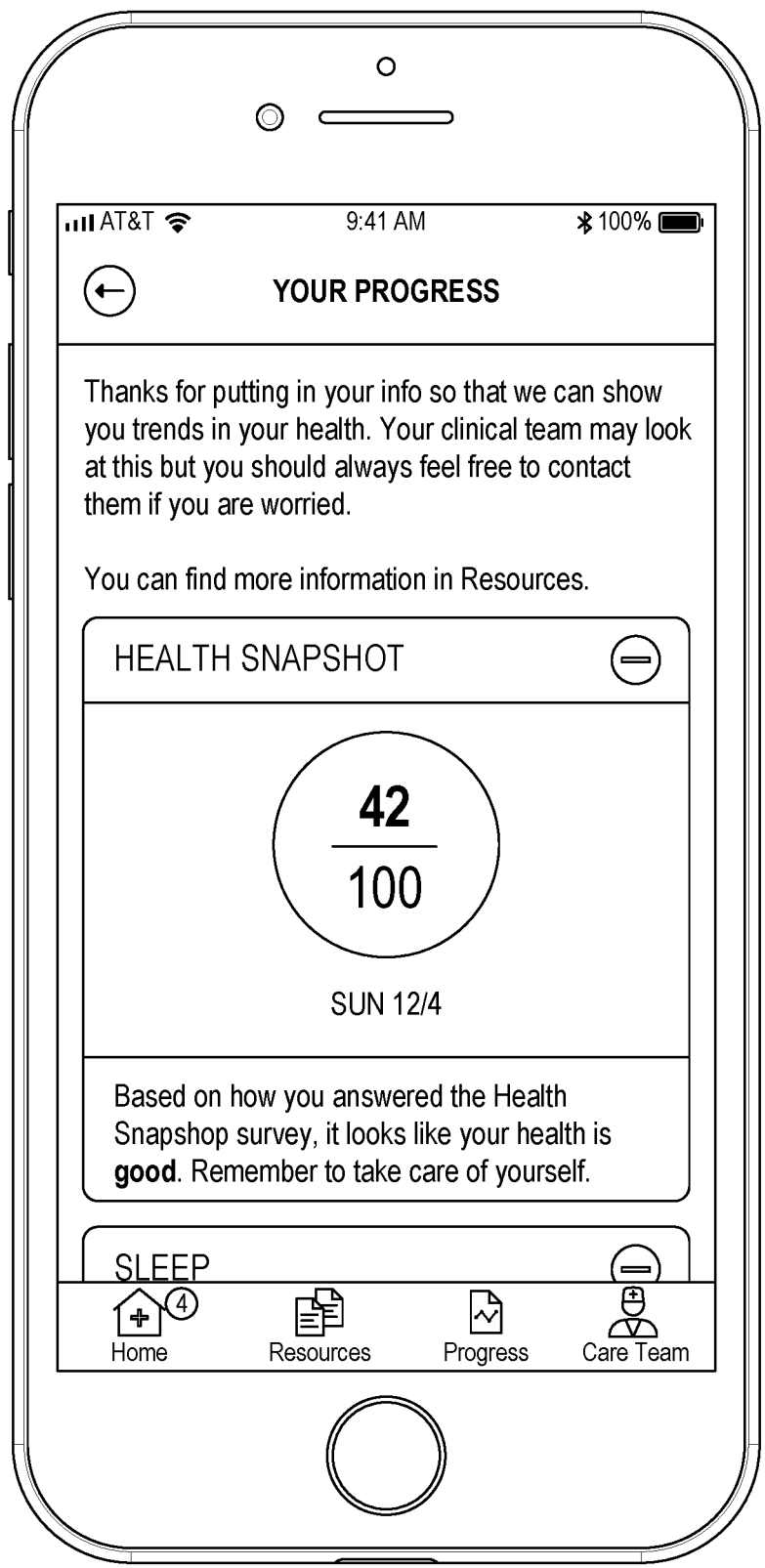
FIG. 13A shows a health snap shot progress hot and communication channel for the patient.
Figure 13B:
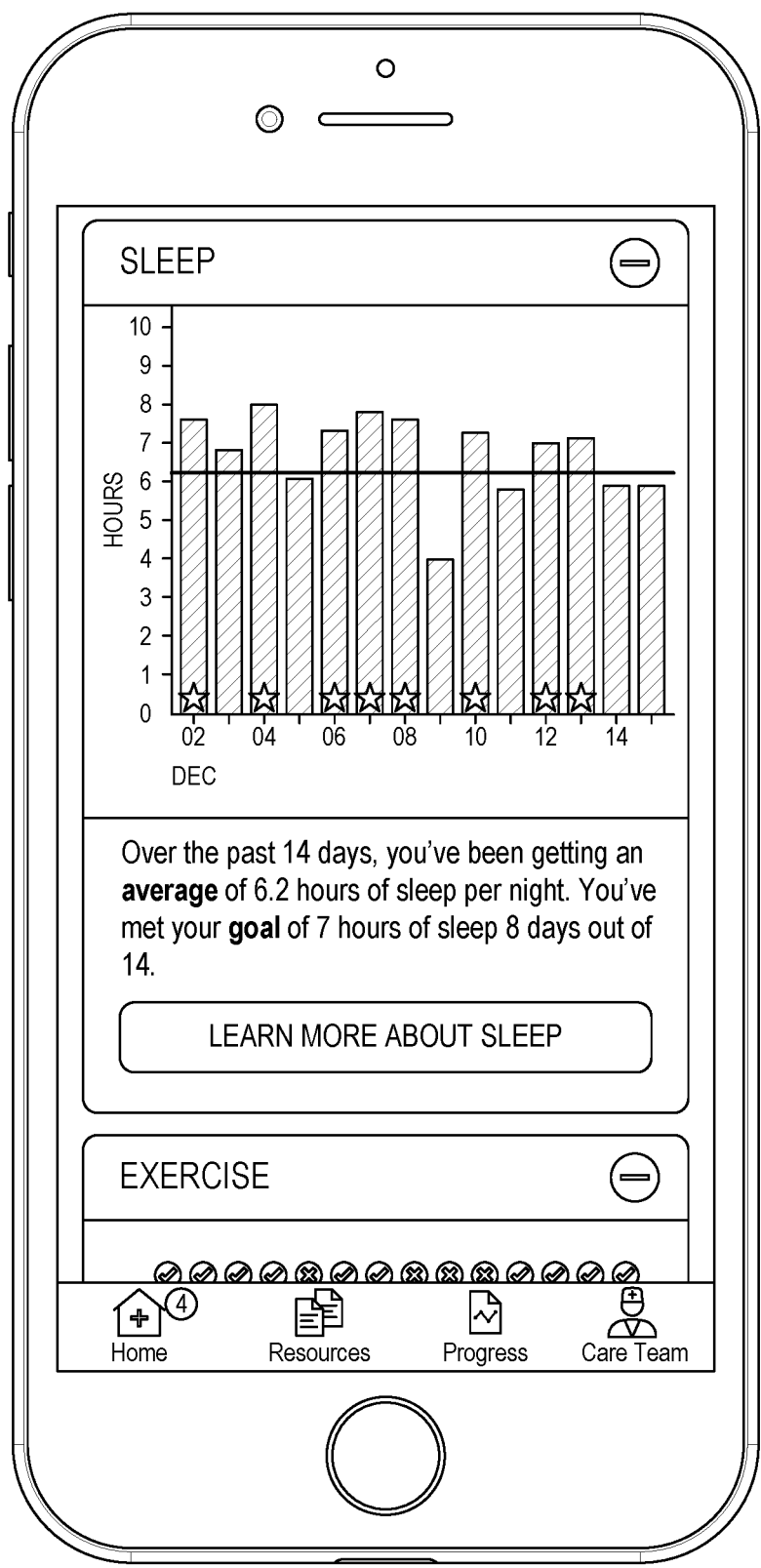
FIG. 13B shows an embodiment such as a sleep pattern.
Figure 14:
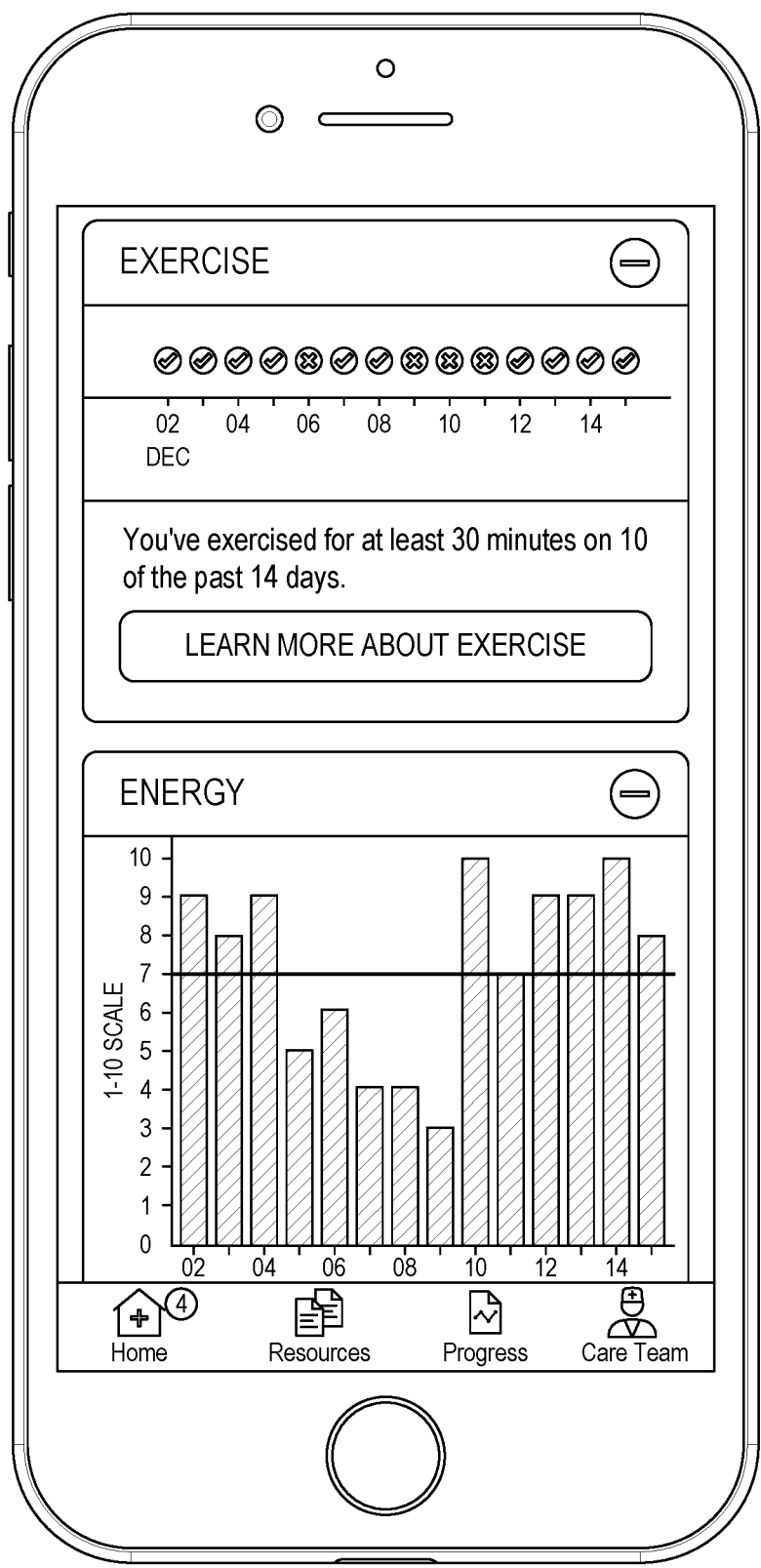
FIG. 14 shows a screenshot of patients exercise routine.

FIG. 11A and FIG. 11B shows patient mobile phone view of their progress. FIG. 12 shows yet another embodiment of the patient progress level. FIG. 13A shows a health snap shot progress hot and communication channel for the patient. FIG. 13B shows an embodiment such as a sleep pattern. FIG. 14 shows a screenshot of patients exercise routine.

Figure 15:
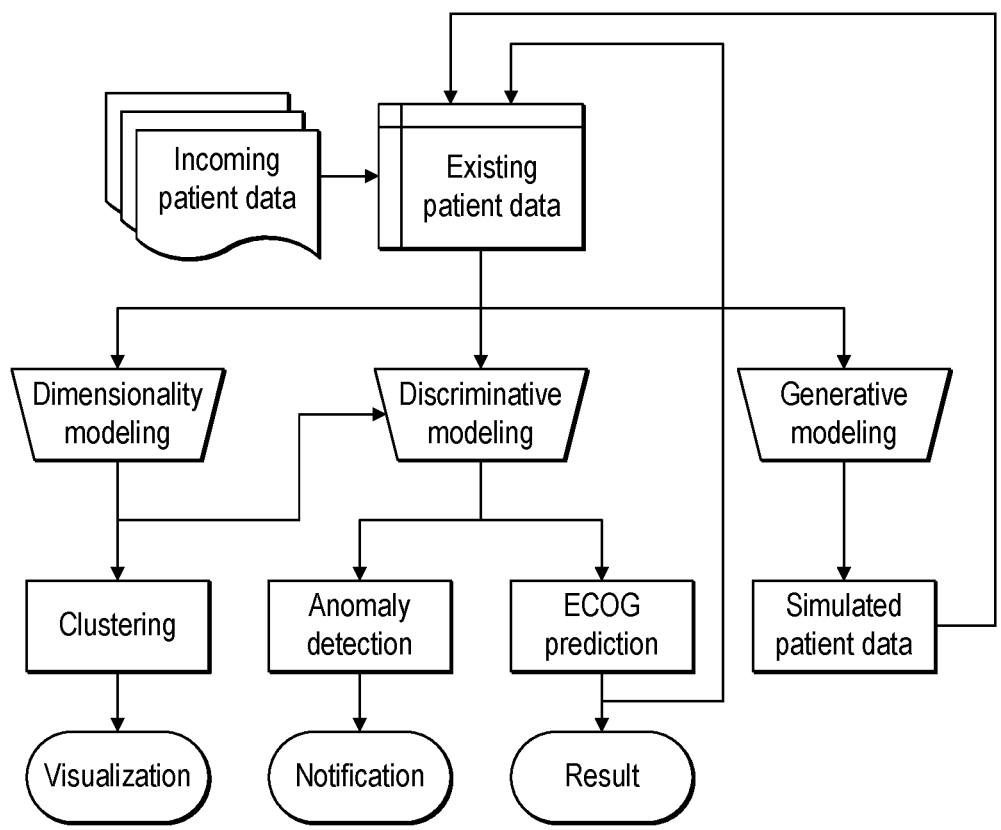
FIG. 15 shows system flow chart, illustrating the interplay between kinds of modeling and sources of data.

FIG. 15 shows a process flow for the application. Data Sources are diverse in nature. Data is aggregated from a variety of sources, including but not limited to survey answers, health data being collected from smartphones/smartwatch and data recorded using mobile phone sensors (e.g.: accelerometer, gyroscope) during predefined tasks (such as sit-and-stand, or gait speed during a fixed time-period).

Data Preprocessing+Aggregation: Data normalization is crucial to machine learning, aiding training stability, preventing divergence, and allowing for larger learning rates. There are various common schemes of normalization, including min-max normalization (in which data is scaled to be within a specified numerical range) and z-score normalization (in which data is scaled to have zero mean and unit variance). Each normalization scheme has unique advantages and disadvantages: for example, min-max normalization is intuitive and flexible, but the presence of outliers can cause it to scale most of the data within a smaller-than-intended range; z-score normalization does not produce data within a target range, but it handles outliers far more robustly.

We normalize each kind of collected data separately; using whichever method best accommodates the data distribution. Data can come from both categorical and numerical sources, each of which must be treated separately. Numerical data—scalar or vector floats—require only normalization before being concatenated together; however, categorical data—e.g., a multiple-choice survey answer—does not require normalization, but must instead be one-hot encoded to avoid the introduction of statistically insignificant inter-category correlation. To do this, integers representing categories (e.g., "3" for "category 3 out of 4") are transformed to binary vectors, with a cell for each possible category. Each cell is 0, except for the cell corresponding to the actual category, which is set to 1. Once one-hot encoded, categorical and numerical vector data can be concatenated together.

Figure 16:
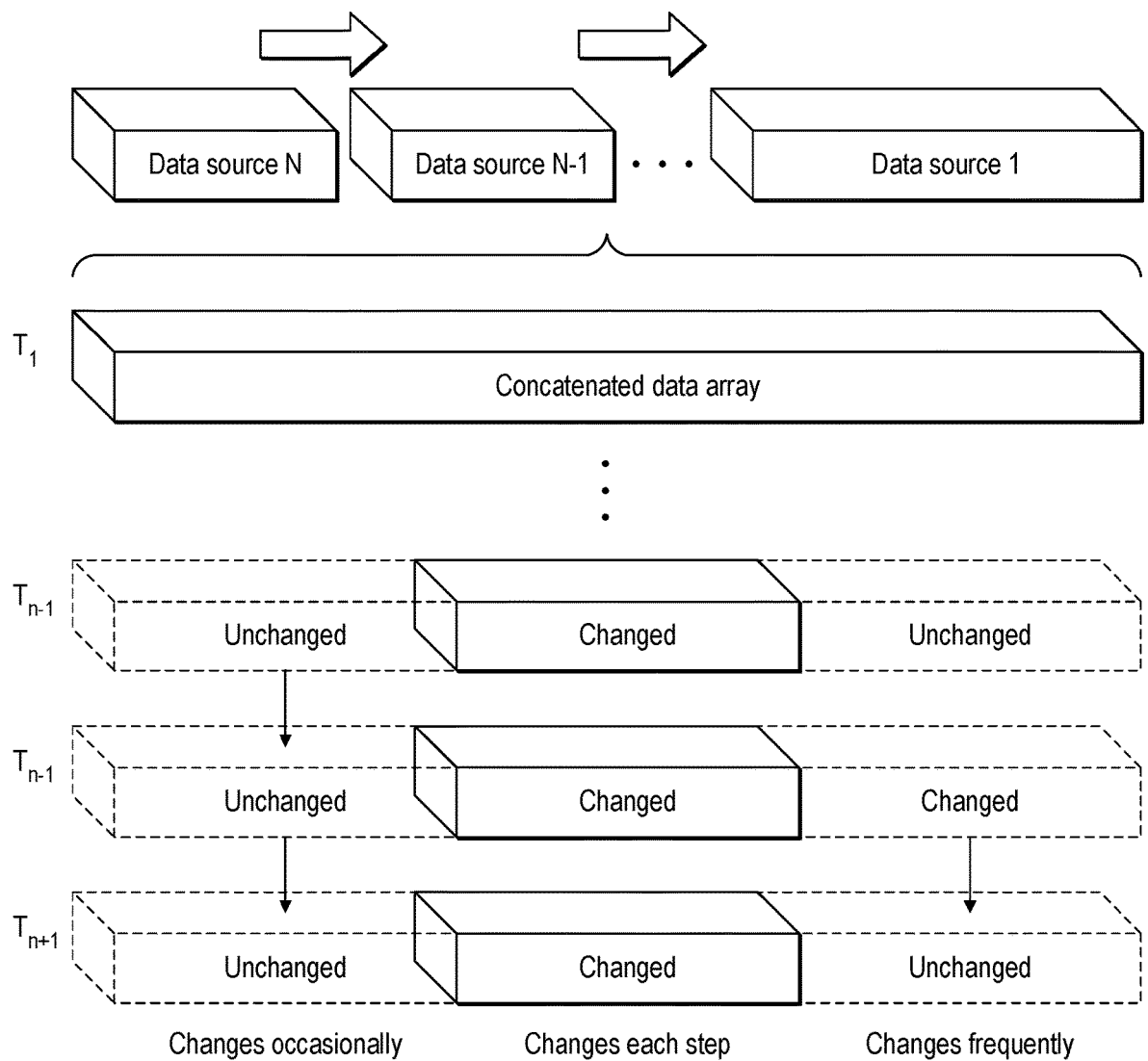
FIG. 16 shows vector data from multiple sources is concatenated into a single data vector; below, one such concatenated vector is created for every "time-step", resulting in a multivariate vector time-series.

We then combine the normalized features into a single "feature vector" per patient per unit of time, with the temporal resolution determined by the most frequently available source of data. Data that does not change with each minimum unit of time is simply repeated across feature vectors until it is updated with new values. This process is illustrated in FIG. 16.

This creates a sort of time series for each patient, containing at every step all of the features we intend to use for downstream Eastern Cooperative Oncology Group (ECOG) analysis. FIG. 15: System flow chart, illustrating the interplay between kinds of modeling and sources of data.

ECOG ratings will be classified or regressed from either the input features directly or from latent representations derived through any of the above unsupervised methods. Prediction will be performed using algorithms including (but not limited to) K-nearest neighbors, support vector machines, and neural networks. A variety of neural-network architectures will be adopted, including convolutional, recurrent, fully-connected, and attention-based. These will be trained with standard modern variants of stochastic gradient descent.

Dimensionality Reduction: Dimensionality reduction offers two key advantages: easier visualization and simplification for downstream processing. Modern approaches to dimensionality reduction (UMAP, t-SNE, or even structured generative methods like beta-VAE) attempt to preserve clustering present in the original, higher-dimensional data manifold. User data will be fed to dimensionality-reduction algorithms as it is collected, or only after aggregation with previously-collected data. Dimensionality reduction is performed at every time-step or across all time, for individual patients or across all patients, enabling the analysis of different kinds of latent structure in the data. For example, a single patient's status may "cluster" around certain common statuses, which may or may not be shared with other patients. Performing a similar dimensionality reduction at each time-step, over all patients, might reveal temporal commonalities in patient status.

By labeling patient state vectors (and their reduced-dimensionality counterparts) with the patient's corresponding ECOG level, it can be assessed whether observed clustering or latent structure in patient state corresponds to a similar level of structure in patient ECOG level. The above approaches do not require ECOG-level labels, except as just mentioned; however, the presence of ECOG labels enables additional levels of analysis, chiefly discriminative and more advanced generative modeling.

Discriminative: The core task of discriminative modeling on patient data will be to determine which collected features (or dimensionally-reduced counterparts) correlate with ECOG level, and leverage those correlations to predict ECOG level from the available patient data. For example, a feed-forward neural network would take as input any patient's data at a single time-step, and attempt to predict, through training, the corresponding ECOG level at that time-step. Such a network would be used to "classify" a patient's ECOG level at any point in time.

A patient-data time-series will be forecasted using approaches as simple as ARIMA or deep-learning approaches like LSTMs or even transformers (potentially with convolutional encoders), enabling the aforementioned ECOG classifier to, in a sense, predict the patient's future ECOG. This could also be done by forecasting the classifier's predicted-ECOG time-series. Finally, anomaly detection, a simpler kind of discriminative modeling, will be leveraged to monitor the concerning changes in patient status over time.

Generative: In deep learning, generative modeling is used in deep learning to model the underlying distribution of a dataset, typically such a way that new data-points can be sampled (or "generated") after training. The most common families of deep neural networks applied to generative modeling are variational autoencoders (VAEs), generative adversarial networks (GANs), and flow-based models.

Generative modeling has been used extensively for data augmentation, the practice of improving data quality to commensurately improve quality of learning on that data. This is accomplished primarily through the supplementation of datasets in "small data" regimes with synthetic samples, and the modification of all samples to optimize learning. Though this is perhaps most common in image domains—GANs capable of producing high-resolution images are prolific in the field of domain adaptation, and in application areas like radiology—the same principles can be applied to tabular and, more pointedly, multidimensional time-series data (as is often done in audio synthesis and related problems). Generative models will be used to model the distribution of patient status over time, enabling the sampling of new data for downstream discriminative models.

Automation—The system leverage our Cerebrum system to automate and execute various data preprocessing and machine learning tasks at scale and in parallel, as described above. Cerebrum is unique in its ability as a cloud-based machine learning platform and advanced analytics system, being specifically designed for patient and clinical-trial-level data. Without Cerebrum, health experts have to perform extremely time intensive work to standardize patient generated data as well as assemble appropriate machine learning systems. Cerebrum's data architecture is based on and embraces established data standards in healthcare and clinical data science. A key component of the system is a proprietary data standardization and normalization technology that ingests vastly varied data types e.g.: smartphone sensor, participant surveys, medical device, contextual, clinical study, and lab data. It utilizes formats such as CSV, JSON, and HL7 for the import, export, and data interchange between various systems. It generates machine learning models to enable pattern detection and algorithm development with the most sophisticated algorithms including deep learning, decision trees, Bayesian, and unsupervised methods such as clustering. To maximize efficiency, Cerebrum's data frame is binary compatible with popular machine learning formats and can support interchange between mainstream data science tools with minimal or no data copying. Furthermore, implementing ECOG with Cerebrum provides the following key advantages:

Allows users of various data science experience levels to utilize the system using an interface which is most appropriate for their skills and preference.

Provides tools to allow power users to work with existing data science tools in a way that they are accustomed to, e.g. Python and R interfaces.

Allows usage of a combination of interfaces for solving a problem.

Provides rich ways of visualizing data.

Allows the computational system to scale while allowing for the ability to control costs of utilized computational resources.

Enables the modular implementation of multiple front-end interfaces, each custom-tailored to specific data analysis and machine learning tasks.

Train machine learning models at scale and in parallel within the cloud.

Determine what can be predicted using a minimal number of inputs.

Using Cerebrum's RESTful interface as a backend, we have designed a high-level web interface that simplifies data exploration, data preparation, and machine learning model building tasks, making it easier for the non-data scientist expert to quickly perform such tasks. Cerebrum streamlines and automates various data preparation stages with a domain-specific language called CML (Cerebrum Modeling Language) and through other easy-to-use graphical user interfaces. Data features, data transformations, and the results of training and running machine learning models are instantly visualized through the integrated UI. And Cerebrum's high-level web interface can be used side-by-side with lower-level programmatic methods. In other applications, Cerebrum has been leveraged to detect patterns in massive patient generated data sets and generate algorithms for disease prediction and digital biomarkers. We use Cerebrum to create standardized representations of different data types specific to ECOG, ensuring highest quality data standards, and to provide the ability to create high-level tools and web interfaces to allow ECOG administrators to rapidly run various analyses, to observe patterns and trends in the data, and to extract key insights.

FIG. 16 shows vector data from multiple sources is concatenated into a single data vector; below, one such concatenated vector is created for every "time-step", resulting in a multivariate vector time-series. Modeling as shown is the multi-dimensional time series generated as described previously can be modeled in both supervised and unsupervised manners, and both generatively and discriminatively.

A high-level illustration of available modeling approaches is shown in FIG. 16. Dimensionality reduction is often a good first step in modeling and can uncover latent, lower-dimensional structure in the data. Feature vectors are clustered—both in time and irrespective of time—using unsupervised methods like K-means, UMAP, and autoencoders with latent-space disentanglement. Variational autoencoders or generative adversarial networks will be trained to model the distribution of the collected data, allowing for the sampling of more (synthetic) data. This would provide training benefits for downstream machine learning.

What is claimed is:

1. A method for integration and analysis for a clinical treatment impact, the method comprising:
    receiving, by a platform, digital biomarker data from a wearable device of a patient;
    forming, by the platform and utilizing a clustered aGgregation (CAG) algorithm, a cluster of mobile devices that includes a mobile device associated with the patient, wherein the forming is based on a determination that sensor data, for each mobile device in the cluster, is within a given threshold range over a predetermined time;
    receiving, by the platform, a subset of the sensor data from the cluster of mobile devices;
    providing a plurality of different types of digital data, obtained at least in part from the mobile device associated with the patient at a particular point in time, as input to one or more neural network models, wherein particular digital data, of the plurality of different types of digital data, is an integer value that represents a category of a plurality of different categories and the particular digital data is transformed into a binary vector before being provided as input to the one or more neural network models,
        wherein the plurality of different types of digital data include at least the subset of sensor data, voice data from the mobile device, and camera data from the mobile device;
    determining, by a prediction unit, a physical activity being performed by the patient at the particular point in time and a situational context for the physical activity being performed by the patient at the particular point in time, wherein
        the determining is based on an output of the one or more neural network models,
        the physical activity is one of a plurality of different types of physical activities, and
        the situational context indicates a type of physical environment, of a plurality of different types of physical environments, in which the physical activity is being performed;
    integrating, by the platform, the digital biomarker data with one or more of the plurality of different types of digital data to generate combined data, wherein the integrating generates a machine learning model and analysis projection using a cloud based analysis engine to integrate the digital biomarker data with the one or more of the plurality of different types of digital data to generate the combined data; and
    generating, by the platform, one or more clinical condition predictions for the patient by utilizing the combined data, the determined activity, and the situational context for the physical activity with one or more prediction algorithms.

2. A system for a digital data integration and analysis for a clinical treatment impact, comprising:
    a platform configured to:
    receive digital biomarker data from wearable device of a patient;
    form, utilizing a clustered aGgregation (CAG) algorithm, a cluster of mobile devices that includes a mobile device associated with the patient, wherein the forming is based on a determination that sensor data, for each mobile device in the cluster, is within a given threshold range over a predetermined time;
    receive a subset of the sensor data from the cluster of mobile devices;
    provide a plurality of different types of digital data, obtained at least in part from the mobile device associated with the patient at a particular point in time, as input to one or more neural network models, wherein particular digital data, of the plurality of different types of digital data, is an integer value that represents a category of a plurality of different categories and the particular digital data is transformed into a binary vector before being provided as input to the one or more neural network models,
        wherein the plurality of different types of digital data include at least the subset of sensor data, voice data from the mobile device, and camera data from the mobile device;
    determine, based on an output of the one or more neural network models, a physical activity being performed by the patient at the particular point in time and a situational context for the physical activity being performed by the patient at the particular point in time, wherein
        the physical activity is one of a plurality of different types of physical activities; integrate the digital biomarker data with one or more of the plurality of different types of digital data to generate combined data, and
        the situational context indicates a type of physical environment, of a plurality of different types of physical environments, in which the physical activity is being performed; and
    generate one or more clinical condition predictions for the patient by utilizing the combined data, the determined physical activity, and the situational context with one or more prediction algorithms.

3. The method of claim 1,
    wherein the machine learning model and analysis projection further utilizes one or more of (1) supervised and unsupervised modelling, (2) dimensionality reduction, (3) discriminative modelling, or (4) and generative modelling.

4. The method of claim 1, further comprising:
integrating the digital biomarker data from the wearable device with different digital biomarker data from other wearable devices associated with the patient to generate combined digital biomarker data.

5. The method of claim 1, further comprising:
utilizing the digital biomarker data in conjunction with existing medical data associated with the patient for management of one or more of a symptom, side effect, a quality of life indicator, or a disease progression for the patient.

6. The method of claim 1, further comprising:
determining (1) one or more changes in a performance status of the patient and (2) one or more changes in a drug treatment provided to the patient throughout a clinical trial.

7. The method of claim 1, wherein the sensor data comprises one or more of accelerometer data or gyroscope data.

8. The method of claim 1, further comprising:
receiving, by the platform, digital medical data associated with the patient; and
integrating the digital biomarker data, the digital data, and the digital medical data to generate the combined data.

9. The method of claim 8, wherein the digital medical data is provided via one or more user interfaces of an application executing on the mobile device associated with the patient.

10. A system for a digital data integration and analysis for a clinical treatment impact, comprising:
a platform configured to:
receive digital biomarker data from wearable device of a patient;
form, utilizing a clustered aGgregation (CAG) algorithm, a cluster of mobile devices that includes a mobile device associated with the patient, wherein the forming is based on a determination that sensor data, for each mobile device in the cluster, is within a given threshold range over a predetermined time;
receive a subset of the sensor data from the cluster of mobile devices;
provide a plurality of different types of digital data, obtained from the mobile device at a particular point in time, as input to one or more neural network models, wherein the plurality of different types of digital data include at least the subset of sensor data, voice data from the mobile device, and camera data from the mobile device;
determine, based on an output of the one or more neural network models, a physical activity being performed by the patient at the particular point in time and a situational context for the physical activity being performed by the patient at the particular point in time, wherein
the physical activity is one of a plurality of different types of physical activities; integrate the digital biomarker data with one or more of the plurality of different types of digital data to generate combined data, and
the situational context indicates a type of physical environment, of a plurality of different types of physical environments, in which the physical activity is being performed; and
generate one or more clinical condition predictions for the patient by utilizing the combined data, the determined physical activity, and the situational context with one or more prediction algorithms.

11. The system of claim 10, wherein the platform is further configured to obtain digital medical data associated with the patient.

12. The system of claim 11, wherein the platform is further configured to integrate the digital biomarker data, the digital data, and the medical data to generate the combined data.

13. The system of claim 11, wherein the digital medical data is provided via one or more user interfaces of an application executing on the mobile device associated with the patient.

14. The system of claim 10, wherein the platform is further configured to:
generate a machine learning model and analysis projection using a cloud based analysis engine, wherein the machine learning model and analysis projection utilizes one or more of (1) supervised and unsupervised modelling, (2) dimensionality reduction, (3) discriminative modelling, or (4) and generative modelling.

15. The system of claim 10, further comprising:
utilize the digital biomarker data in conjunction with existing medical data for management of one or more of a symptom, a side effect, a quality of life indicator, or a disease progression.

16. The system of claim 10, wherein the sensor data comprises one or more of accelerometer data or gyroscope data.

* * * * *